United States Patent [19]

Berges

[11] 4,101,656

[45] Jul. 18, 1978

[54] 7β-ACYLAMINO-3-(ALKANESUL-FONAMIDOALKYL SUBSTITUTED TETRAZOLYLTHIOMETHYL) CEPHALOSPORINS, ANTIBACTERIAL COMPOSITIONS CONTAINING THEM AND METHODS OF TREATING BACTERIAL INFECTIONS WITH THEM

[75] Inventor: David A. Berges, Wayne, Pa.

[73] Assignee: Smithkline Corporation, Philadelphia, Pa.

[21] Appl. No.: 704,141

[22] Filed: Jul. 12, 1976

[51] Int. Cl.$^2$ .................. A61K 31/545; C07D 501/54; C07D 501/56
[52] U.S. Cl. .............................. 424/246; 260/308 D; 544/21; 544/26; 544/27
[58] Field of Search .................... 260/243 C; 424/246; 544/21, 26, 27

[56] References Cited

U.S. PATENT DOCUMENTS 3,929,779  12/1975  Bickel et al. ..................... 260/243 C

FOREIGN PATENT DOCUMENTS 818,209   11/1974  Belgium.
2,415,402 10/1974  Fed. Rep. of Germany ... 260/243 C
2,514,322 10/1975  Fed. Rep. of Germany.

*Primary Examiner*—Donald G. Daus
*Assistant Examiner*—Diana G. Rivers
*Attorney, Agent, or Firm*—Janice E. Williams; William H. Edgerton; Alan D. Lourie

[57] ABSTRACT

The compounds of this invention are cephalosporins having various acyl substituents at the 7-position and an alkanesulfonamidoalkyl substituted tetrazolylthiomethyl group at the 3-position of the cephem nucleus and intermediates for the preparation thereof. The 7-acylated compounds have antibacterial activity.

30 Claims, No Drawings

7β-ACYLAMINO-3-(ALKANESULFONAMIDOALKYL SUBSTITUTED TETRAZOLYLTHIOMETHYL) CEPHALOSPORINS, ANTIBACTERIAL COMPOSITIONS CONTAINING THEM AND METHODS OF TREATING BACTERIAL INFECTIONS WITH THEM

This invention relates to a new series of cephalosporin compounds which have antibacterial activity when administered parenterally and to intermediates for the preparation thereof. In particular, the structures of the biologically active cephalosporin compounds of this invention are characterized by having an alkanesulfonamidoalkyl substituted tetrazolylthiomethyl group at the 3-position of the cephem nucleus. Also, this invention extends to methods and compositions for treating certain bacterial infections using these new compounds as well as to certain chemical intermediates and methods for preparing the compounds described hereafter.

The compounds of this invention are represented by the following structural formula:

$$R^1-N(H)-\text{[β-lactam-cephem]}-CH_2S-\text{tetrazole}-(CH_2)_n-NHSO_2R^2$$

FORMULA I in which:

W is hydrogen or methoxy;

$R^1$ is an acyl group selected from the group consisting of:

$$X-CH(A)-C(=O)-, \quad Y-CH_2-C(=O)- \quad \text{and} \quad Z-S(O)_m-CH_2-C(=O)-$$

where:

X is thienyl, phenyl or phenyl monosubstituted with hydroxy, hydroxymethyl, formamido or ureido;

A is $NH_2$, OH, COOH, $SO_3H$ or formyloxy;

Y is cyano, sydnone, pyridone, thienyl or tetrazolyl;

Z is methyl, trifluoromethyl, trifluoroethyl, pyridyl or cyanomethyl;

m is zero to two;

n is two to five; and $R^2$ is alkyl of from one to four carbon atoms, or a non-toxic pharmaceutically acceptable salt or hydrate thereof.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such esters are included within the scope of this invention.

A group of compounds of this invention is represented by Formula I where n is two.

Another group of compounds of this invention comprises those compounds of Formula I where n is two and $R^2$ is methyl.

Yet another group consists of the compounds of Formula I where n is two, $R^2$ is methyl, W is hydrogen and $$X-CH(A)-C(=O)-.$$

A selected group of the compounds of Formula I are those where n is two, $R^2$ is methyl, W is hydrogen, $R^1$ is $$X-CH(A)-C(=O)-,$$

X is phenyl or hydroxyphenyl and A is $NH_2$ or OH.

Representative 7-acyl substituents ($R^1NH-$) of the compounds of Formula I are listed below:

α-hydroxyphenylacetamido
α-aminophenylacetamido
α-amino-4-hydroxyphenylacetamido
trifluoromethylthioacetamido
2,2,2-trifluoroethylsulfinylacetamido
2,2,2-trifluoroethylthioacetamido
cyanoacetamido
α-carboxythienylacetamido
α-carboxyphenylacetamido
α-sulfophenylacetamido
methylsulfonylacetamido
cyanomethylthioacetamido
3-sydnoneacetamido
1-tetrazolylacetamido
2-thienylacetamido
4-pyridylthioacetamido.

Some examples of the compounds of this invention are 7β-D-mandelamido-3-[1-(2-methanesulfonamidoethyl)-tetrazol-5-ylthiomethyl]-3-cephem-4-carboxylic acid, 7β-(2-thienylacetamido)-3-[1-(2-methanesulfonamidoethyl)-tetrazol-5-ylthiomethyl]-3-cephem-4-carboxylic acid, 7β-(1-tetrazolylacetamido)-3-[1-(2-methanesulfonamidoethyl)tetrazol-5-ylthiomethyl]-2-cephem-4-carboxylic acid, 7β-cyanomethylthioacetamido-3-[1-(2-methanesulfonamidoethyl) tetrazol-5-ylthiomethyl]-3-cephem-4-carboxylic acid, 7β-(D-α-aminophenylacetamido)-3-[1-(2-methanesulfonamidoethyl)tetrazol-5-ylthiomethyl]-3-cephem-4-carboxylic acid, 7β-(D-α-amino-4-hydroxyphenylacetamido)-3-[1-(2-methanesulfonamidoethyl)tetrazol-5-ylthiomethyl]-3-cephem-4-carboxylic acid, 7β-D-mandelamido-7α-methoxy-3-[1-(2-methanesulfonamidoethyl)tetrazol-5-ylthiomethyl]-3-cephem-4-carboxylic acid, 7β-(D-α-aminophenylacetamido)-7α-methoxy-3-[1-(2-methanesulfonamidoethyl)tetrazol-5-ylthiomethyl]-3-cephem-4-carboxylic acid, 7α-methoxy-7β-trifluoromethylthioacetamido-3-[1-(2-methanesulfonamidoethyl)-tetrazol-5-ylthiomethyl]-3-cephem-4-carboxylic acid, and 7α-methoxy-7β-(2-thienylacetamido)-3-[1-(2-methanesulfonamidoethyl)tetrazol-5-ylthiomethyl]-3-cephem-4-carboxylic acid.

Cephalosporin derivatives having 7-acyl substituents as defined above are well documented in the prior art. Substitution by variously substituted S-heterocyclic-thiomethyl groups, including tetrazolylthiomethyl, at the 3-position of the cephem nucleus is also known. German Offenlegungsschrift No. 2,415,402 discloses 7-(acyl or amino)-cephalosporins having a N-containing heterocyclicthiomethyl group at the 3-position substituted by, inter alia, an acylaminoalkyl group. Belgian Patent No. 818,209 discloses 7-(thiosubstituted acylamino)-3-heterocyclicthiomethylcephalosporins where the heterocyclic moiety is substituted by, among others, $-SO_2R_1$ where $R_1$ is alkyl, amino, or hydroxy. In addition, German Offenlegungsschrift No. 2,514,322 discloses 7-(α-N-substituted phenylglycinamido)-3-heterocyclicthiomethylcephalosporins which may be substituted on the heterocyclic ring by, inter alia, a sulfoalkyl group. No references to cephalosporin compounds containing the 3-(alkanesulfonamidoalkyl substituted tetrazolyl)thiomethyl moiety disclosed herein are believed to be known to the art.

When W is hydrogen, the compounds of Formula I are preferably prepared by acylating 7β-aminocephalosporanic acid (7-ACA) with an appropriate acylating agent, suitably protected as necessary, and then displacing the 3-acetoxy group with the desired alkanesulfonamidoalkyltetrazole thiol of the formula:

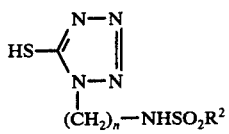

FORMULA II in which:

n is two to five; and $R^2$ is alkyl of from one to four carbon atoms, with subsequent removal of the protective group(s). When certain acylating agents are used, for example activated and protected derivatives of mandelic acid, it is preferable to remove the protecting group from the 7-sidechain prior to displacement.

The carboxylic acid group of the acylating agent in the first step of this reaction, the 7-acylation, is activated by any of the standard methods such as conversion to the mixed anhydride, acid chloride, acid imidazole or activated ester. In addition, a reagent such as dicyclohexylcarbodiimide can be used provided that the carboxyl group on the cephem nucleus is protected with an easily removable protecting group such as a benzhydryl, t-butyl, trichloroethyl, benzyl, benzyloxymethyl, p-methoxybenzyl or p-nitrobenzyl ester. When A is $NH_2$, the α-amino group of the acylating agent is, preferably, protected prior to acylation with an easily removable protective group known in the art such as t-butoxycarbonyl, trichloroethoxycarbonyl, benzyloxycarbonyl, the methyl acetoacetate adduct or similar groups commonly used in the synthesis of peptides.

Alternatively, and preferably when W is methoxy, the compounds of Formula I are prepared by acylation, as described above, of an appropriate 7β-amino-3-(alkanesulfonamidoalkyl substituted tetrazolylthiomethyl)cephalosporin nucleus of Formula III:

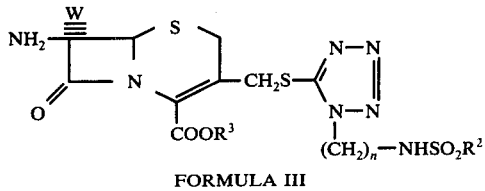

FORMULA III in which:

W is hydrogen or methoxy;

n is two to five;

$R^2$ is alkyl of from one to four carbon atoms; and $R^3$ is hydrogen or a protecting ester group, with an appropriate acylating agent followed by removal of the protective groups when present.

The protective groups can be removed according to methods well known to the art, such as with trifluoroacetic acid when t-butyl or t-butoxycarbonyl protective groups are used. The resulting salt is converted to the zwitterionic product or to the free acid by means of a basic ion exchange resin such as polystyrene-amine ion exchange resin (Amberlite IR-45) or else by basification of an aqueous solution of the salt.

The acylating agents used as starting materials are either known or prepared by known methods.

The 7β-amino-3-alkanesulfonamidoalkyltetrazolylthiomethyl cephalosporin starting materials of Formula III where W is hydrogen are prepared by reaction of 7β-aminocephalosporanic acid and a substituted tetrazole thiol of Formula II and then esterifying.

When W is methoxy, the 7β-amino-7α-methoxy cephalosporin nuclei of Formula III are prepared by reaction of the corresponding 7β-amino-3-(substituted tetrazolylthiomethyl)-cephalosporin where W is hydrogen and $R^3$ is a protecting ester group such as a t-butyl group with 3,5-di-t-butyl-4-hydroxybenzaldehyde with azeotropic removal of water. Subsequent treatment of the product thus formed with lead dioxide and reaction of the oxidized intermediate with methanol followed by cleavage of the imine function with, for example, Girard reagent T (trimethylaminoacetohydrazide chloride), followed by removal of the protective group(s) as desired gives the compounds of Formula III.

The alkanesulfonamidoalkyltetrazole thiols of Formula II are prepared by reaction of the corresponding 1-aminoalkyl-5-(2,4-dinitrophenylthio)tetrazole compounds, prepared from 2,4-dinitrofluorobenzene and a 1-acetamidoalkyltetrazole-5-thiol followed by acid hydrolysis of the acetamido moiety, with an alkanesulfonyl halide such as methanesulfonyl chloride with subsequent cleavage of the 2,4-dinitrophenyl protecting group. The 1-acetamidoalkyltetrazole-5-thiols are prepared by reaction of an acetamidoalkyldithiocarbamate such as methyl 2-acetamidoethyldithiocarbamate with an azide such as sodium azide. The acetamidoalkyldithiocarbamates are prepared by treatment of a N-aminoalkylacetamide such as N-(2-aminoethyl)-acetamide with carbon disulfide and an alkyl halide such as methyl iodide in the presence of a base such as triethylamine.

The compounds of Formulas II and III are also considered as objects of this invention.

Certain compounds of this invention are capable of forming salts with, for example, the alkali metals such as sodium or potassium, the alkaline earth metals such as calcium or with the ammonium cation. When A is $NH_2$, the compounds can exist as the zwitterion or as either an acid or base salt. These salts are prepared by standard methods using a wide variety of non-toxic pharmaceutically acceptable acids and bases known in the art and are also considered as objects of this invention.

The compounds of Formula I and salts thereof may also exist as hydrates or solvates. All such hydrates, solvates and fractions thereof are comnsidered as being encompassed within the scope of this invention.

It will be recognized that due to the asymmetric α-carbon atom in the 7-acetamido group of Formula I when $R^1$ is

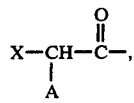

optical isomers will exist. Racemic or resolved products are obtained depending upon whether a racemic or resolved sidechain acid is used as an acylating agent. The resolved sidechain acids are readily obtained from the racemic compounds by resolution according to well known methods, including fractional crystallization of a salt formed with an optically active acid or base. All of the isomers, including separated isomers and mixtures thereof, are included within the scope of this invention.

The compounds of Formula I have exceptional antibacterial activity against both Gram-positive and Gram-negative organisms. Minimum inhibitory concentrations (MIC's) range from 0.2 to >200 μg/ml in in vitro testing. Test results for the compound 7β-D-mandelamido-3-[1-(2-methanesulfonamidoethyl)tetrazol-5-ylthiomethyl]-3-cephem-4-carboxylic acid sodium salt hydrate (Compound A) are given below:

| | MIC (μg/ml) | |
|---|---|---|
| Bacteria | Compound A | Cefazolin |
| S. aureus HH 127 | 3.1, 1.6 | 0.4, 0.4 |
| S. aureus SK 23390 | 0.8, 0.4 | 0.2, 0.2 |
| S. villaluz SK 70390 | 6.3, 25 | 25, 100 |
| Strep. faecalis HH 34358 | 25, 12.5 | 6.3, 6.3 |
| E. coli SK 12140 | 0.8, 0.8 | 0.8, 0.8 |
| E. coli HH 33779 | 1.6, 0.8 | 1.6, 1.6 |
| Kleb. pneumo. SK 4200 | 0.4, 0.4 | 1.6, 1.6 |
| Kleb. pneumo. SK 1200 | 0.4, 0.4 | 0.8, 0.8 |
| Salmonella ATCC 12176 | 0.4, 0.4 | 0.8, 0.8 |
| Shigella HH 117 | 0.2 | 0.4 |
| Pseudo. aerug. HH 63 | >200, >200 | >200, >200 |
| Serratia marc. ATCC 13880 | 6.3, 3.1 | >200, >200 |
| Proteus morgani 179 | 1.6, 0.8 | 200, 200 |
| Entero aerog. ATCC 13048 | 1.6, 0.8 | 1.6, 1.6 |
| Entero. cloacae HH 31254 | 0.8, 0.8 | 0.8, 0.8 |
| Proteus mirabilis 444 | 0.8 | 3.1 |

In the in vivo mouse protection test, 7β-D-mandelamido-3-[1-(2-methanesulfonamidoethyl)tetrazol-5-ylthiomethyl]-3-cephem-4-carboxylic acid sodium salt hydrate exhibited $ED_{50}$'s at 0.39 mg/kg against E. coli 12140 and 2.44 mg/kg against Kleb. pneumo. 4200 upon subcutaneous injection; cefazolin gave results of 4 mg/kg against E. coli 12140 and 11.3 mg/kg against Kleb. pneumo. 4200 upon subcutaneous administration.

Pharamceutical compositions having antibacterial activity which comprise a pharmaceutical carrier containing an active but non-toxic quantity of a compound of Formula I as well as methods of combatting bacterial infections by administering such a composition to an infected host in a non-toxic amount sufficient to combat such infections are also objects of this invention. The administration may be orally or by parenteral injection such as subcutaneously, intramuscularly or intravenously. The injection of suitable prepared sterile solutions or suspensions containing an effective, non-toxic amount of the new cephalosporin compound is the preferred route of administration.

The compounds of Formula I are formulated and administered in the same manner as other cephalosporins. The dosage regimen comprises administration, preferably by injection, of an active but non-toxic quantity of a compound of Formula I selected from the dosage unit range of from 100 to 1000 mg with the total daily dosage regimen being from 400 mg to 6 g. The precise dosages are dependent upon the age and weight of the subject and on the infection being treated and can be determined by those skilled in the art based on the data disclosed herein compared with that available to the art attained with known cephalosporins.

The following examples illustrate the invention but are not to be construed as limiting the scope thereof. Temperatures are in degrees Centigrade (0° C) unless otherwise stated.

EXAMPLE 1

7β-D-Mandelamido-3-[1-(2-methanesulfonamidoethyl)-tetrazol-5-ylthiomethyl]-3-cephem-4-carboxylic acid To a solution of 20.4 g (0.20 mol) of N-(2-aminoethyl-)acetamide in 200 ml of 95% ethanol was added 27.9 ml (0.20 mol) of triethylamine and 12.0 ml (0.20 mol) of carbon disulfide. The exothermic reaction reached reflux and then cooled to ambient temperature over a 1.5 hour period. Methyl iodide (28.4 g, 0.20 mol) was then added which again produced an exothermic reaction. After an additional 1.75 hours the reaction mixture was evaporated to dryness and the solid residue was dissolved in 200 ml of water. The aqueous solution was extracted twice with 250 ml portions of ethyl acetate. The extracts were combined, shaken with solid sodium thiosulfate, dried (MgSO₄) and evaporated to dryness to give methyl 2-acetamidoethyldithiocarbamate.

To a solution of 38.4 g (0.198 mol) of methyl 2-acetamidoethyldithiocarbamate in 100 ml of 95% ethanol was added a solution of 13.5 g (0.208 mol) of sodium azide in 100 ml of water. The reaction mixture was refluxed for 24 hours then cooled and concentrated under reduced pressure to about half volume. The solution was cooled to 15° and 50 ml of 6N sulfuric acid was added. The acidic solution was filtered and the filtrate was concentrated to about 100 ml and chilled at 5° to induce crystallization of 1-(2-acetamidoethyl)tetrazole-5-thiol which was collected by filtration, mp 139°–139.5°. Additional amounts of the product were obtained by continuous extraction of the filtrate with ethyl acetate.

A solution of 9.3 g (0.050 mol) of 2.4-dinitrofluorobenzene in 50 ml of acetone was added to a solution of 9.35 g (0.050 mol) of 1-(2-acetamidoethyl)tetrazole-5-thiol and 6.85 ml (0.050 mol) of triethylamine in 100 ml of acetone and the reaction mixture was stirred for 1 hour. The solid material was collected by filtration and recrystallized from acetonitrile to give 1-(2-acetamidoethyl)-5-(2,4-dinitrophenylthio)tetrazole, mp 197°–198°.

A mixture of 6.5 g (0.02 mol) of 1-(2-acetamidoethyl)-5-(2,4-dinitrophenylthio)tetrazole, 100 ml of 12 N hydrochloric acid and 100 ml of 95% ethanol was refluxed for 4.5 hours. The mixture was evaporated to dryness to give a gummy residue which crystallized upon addition of ethanol to give 1-(2-aminoethyl)-5-(2,4-dinitrophenylthio)tetrazole hydrochloride, mp 217°–219° (d).

To a suspension of 4.9 g (14.1 mmol) of 1-(2-aminoethyl)-5-(2,4-dinitrophenylthio)tetrazole hydrochloride in 100 ml of pyridine was added 1.5 ml (2.2 g, 19.2 mmol) of methanesulfonyl chloride. The mixture was stirred for 1.5 hours, then an additional 0.5 ml of methanesulfonyl chloride was added and the mixture was stirred another hour. The pyridine was removed by evaporation and the residue was dissolved in a small volume of dimethylformamide. Water was added to the solution and the resulting precipitate was collected by filtration, washed with watr and air dried. The precipitate was dissolved in a minimum amount of dimethylformamide and the solution was diluted with ethyl acetate and treated with Darco G-60. The mixture was filtered and evaporated to dryness to give a syrupy residue which was crystallized from ethyl acetate to give 5-(2,4-dinitrophenylthio)-1-(2-methanesulfonamidoethyl)tetrazole.

$C_{10}H_{11}N_7O_6S_2$

Calculated: 30.85% C; 2.85% H; 25.18%; N. Found: 31.08% C; 3.09% H; 25.17% N.

5-(2,4-Dinitrophenylthio)-1-(2-methanesulfonamidoethyl)tetrazole (4.46 g, 11.5 mmol) was added to 60 ml of 5% sodium methoxide in methanol. After 1 hour, water was added and the solid material was removed by filtration. The filtrate was concentrated in vacuo and 3N hydrochloric acid was added to the residue to bring the pH to 1.4. The acidic solution was filtered and the filtrate was extracted twice with ethyl acetate. The extracts were combined and concentrated to give a residue which crystallized upon addition of ethyl acetate to give 1-(2-methanesulfonamidoethyl)tetrazole-5-thiol, mp 131°–132°.

$C_4H_9N_5O_2S_2$

Calculated: 21.52% C; 4.06% H; 31.37% N. Found: 21.61% C; 4.19% H; 31.63% N.

a mixture of 4.52 g (10.0 mmol) of 7β-D-mandelamidocephalosporanic acid sodium salt 1.3 hydrate, 1.70 g (7.5 mmol) of 1-(2-methanesulfonamidoethyl)tetrazole-5-thiol and sufficient sodium bicarbonate to bring the pH to 6.8 was heated at 68° for 3 hours. After cooling to ambient temperature, the pH of the reaction mixture was adjusted to 1.8 by addition of 3N hydrochloric acid. The resulting gummy material was removed and dissolved in acetone. Ethyl acetate was added and the precipitated solid was collected by filtration and discarded. Ether was added to the filtrate to precipitate the title compound which was collected and dissolved in methanol. The methanol solution was treated with sodium methoxide solution until pH 7.0 then isopropanol was added. The resulting precipitate was collected, dissolved in water and lyophilized to give the title compound as its sodium salt.

$C_{20}H_{22}N_7O_7S_3 \cdot Na \cdot 0.75 \ H_2O$

Calculated: 39.69% C; 3.91% H; 16.20% N. Found: 40.11% C; 3.91% H; 15.11% N.

An aqueous solution of 7β-D-mandelamido-3-[1-(2-methanesulfonamidoethyl)tetrazol-5-ylthiomethyl]-3-cephem-4-carboxylic acid sodium salt is acidified with 3N hydrochloric acid to pH 2.5 and extracted with ethyl acetate. The extract is dried over anhydrous magnesium sulfate and evaporated to dryness to give the title compound.

EXAMPLE 2

7β-(D-α-Aminophenylacetamido)-3-[1-(2-methanesulfonamidoethyl)tetrazol-5-ylthiomethyl]-3-cephem-4-carboxylic acid A solution of 7.58 g (0.015 mol) of 7β-(D-α-t-butoxycarbonylaminophenylacetamido)cephalosporanic acid, 2.27 g (0.01 mol) of 1-(2-methanesulfonamidoethyl)tetrazole-5-thiol and 2.52 g (0.03 mol) of sodium bicarbonate in 125 ml of water is stirred at 60° for 5 hours while maintaining the pH at 7.0-7.2 by addition of sodium bicarbonate. The mixture is cooled and extracted with ethyl acetate. The aqueous phase is acidified to pH 2.5 with 3N hydrochloric acid and the acidic solution is extracted again with ethyl acetate. This extract is dried (MgSO₄), filtered and evaporated to dryness to give 7β-(D-α-t-butoxycarbonylaminophenylacetamido)-3-[1-(2-methanesulfonamidoethyl)-tetrazol-5-ylthiomethyl]-3-cephem-4-carboxylic acid.

7β-(D-α-t-Butoxycarbonylaminophenylacetamido)-3-[1-(2-methanesulfonamidoethyl)tetrazol-5-ylthiomethyl]-3 -cephem-4-carboxylic acid (ca. 1 g) is stirred at 25° with 25 ml of trifluoroacetic acid and 25 ml of 1,3-dimethoxybenzene for 2.25 hours. The mixture is evaporated to dryness in vacuo, ether is added to the residue and the precipitate is collected, washed with ether, stirred in acetonitrile for 2 hours and then collected and dried in vacuo to give the title compound as its trifluoroacetic acid salt. The salt is dissolved in water and the solution is stirred with IR-45 ion exchange resin then lyophilized to give the title compound.

EXAMPLE 3

Reaction of the N-t-butoxycarbonyl derivative of the following cephalosporanic acids:
7β-amino-4-hydroxyphenylacetamido)cephalosporanic acid
7β-(α-amino-4-formamidophenylacetamido)cephalosporanic acid
7β-(α-amino-3-formamidophenylacetamido)cephalosporanic acid
7β-(α-amino-4-ureidophenylacetamido)cephalosporanic acid
7β-(α-amino-3-ureidophenylacetamido)cephalosporanic acid
7β-(α-amino-4-hydroxymethylphenylacetamido)cephalosporanic acid
with 1-(2-methanesulfonamidoethyl)tetrazole-5-thiol as described in the procedure of Example 2 followed by removal of the protective group and conversion of the trifluoroacetic acid salt to the free acid as described therein gives the following compounds of this invention:
7β-(α-amino-4-hydroxyphenylacetamido)-3-[1-(2-methanesulfonamidoethyl)tetrazol-5-ylthiomethyl]-3-cephem-4-carboxylic acid
7β-(α-amino-4-formamidophenylacetamido)-3-[1-(2-methanesulfonamidoethyl)tetrazol-5-ylthiomethyl]-3-cephem-4-carboxylic acid
7β-(α-amino-3-formamidophenylacetamido)-3-[1-(2-methanesulfonamidoethyl)tetrazol-5-ylthiomethyl]-3-cephem-4-carboxylic acid
7β-(α-amino-4-ureidophenylacetamido)-3-[1-(2-methanesulfonamidoethyl)tetrazol-5-ylthiomethyl]-3-cephem-4-carboxylic acid 7β-(α-amino-3-ureidophenylacetamido-3[1(2-methanesulfonamidoethyl)tetrazol-5-ylthiomethyl]-3-cephem-4-carboxylic acid 7β-(α-amino-4-hydroxymethylphenylacetamido)-3-[1-(2-methanesulfonamidoethyl)tetrazole-5-ylthiomethyl]-3-cephem-4-carboxylic acid.

EXAMPLE 4

7β-(4-Hydroxymandelamido)-3-[1-(2-methanesulfonamidoethyl)tetrazol-5-ylthiomethyl]-3-cephem-4-carboxylic acid is prepared by reaction of 7β-(4-hydroxymandelamido)cephalosporanic acid sodium salt and 1-(2-methanesulfonamidoethyl)tetrazole-5-thiol sodium salt as described in the procedure of Example 1 followed by conversion of the product sodium salt to the free acid as described therein.

EXAMPLE 5

When the sodium salt of a cephalosporanic acid listed below:
7β-(3-sydnoneacetamido)cephalosporanic acid
7β-(2-thienylacetamido)cephalosporanic acid
7β-(1-tetrazolylacetamido)cephalosporanic acid
is reacted with 1-(2-methanesulfonamidoethyl)tetrazole-5-thiol and sodium bicarbonate by the procedure described in Example 1 and the product is converted to the free acid as described therein, the following compounds of this invention are obtained, respectively:
7β-(3-sydnoneacetamido)-3-[1-(2-methanesulfonamidoethyl)tetrazol-5-ylthiomethyl]-3-cephem-4-carboxylic acid
7β-(2-thienylacetamido)-3-[1-(2-methanesulfonamidoethyl)tetrazol-5-ylthiomethyl]-3-cephem-4-carboxylic acid
7β-(1-tetrazolylacetamido)-3-[1-(2-methanesulfonamidoethyl)tetrazol-5-ylthiomethyl]-3-cephem-4-carboxylic acid.

EXAMPLE 6

7β-Trifluoromethylthioacetamido-3-[1-(2-methanesulfonamidoethyl)tetrazol-5-ylthiomethyl]-3-cephem-4-carboxylic acid A solution of 2.27 g (10.0 mmol) of 1-(2-methanesulfonamidoethyl)tetrazole-5-thiol, 0.840 g of sodium bicarbonate and 5.45 g (12.5 mmol) of 7β-trifluoromethylthioacetamidocephalosporanic acid sodium salt in 60 ml of water is stirred at 70°–75° for 5 hours while maintaining the pH at 6.8 by addition of 5% aqueous sodium carbonate solution. The reaction mixture is cooled and diluted with water. Ethyl acetate is added and the mixture is acidified to pH 2.0 with 6N hydrochloric acid. The combined aqueous phases are further extracted with ethyl acetate and the extracts are dried ($MgSO_4$) and evaporated to dryness to give the title compound.

EXAMPLE 7

Reaction of the sodium salt of a cephalosporanic acid listed below:
7β-(2,2,2-trifluoroethylthioacetamido)cephalosporanic acid
6β-trifluoromethylsulfinylacetamidocephalosporanic acid
with 1-(2-methanesulfonamidoethyl)tetrazole-5-thiol and sodium bicarbonate as described in the procedure of Example 6 gives the following compounds of this invention as final products:

7β-(2,2,2-trifluoroethylthioacetamido)-3-[1-(2-methanesulfonamidoethyl)tetrazol-5-ylthiomethyl]-3-cephem-4-carboxylic acid
7β-trifluoromethylsulfinylacetamido-3-[1-(2-methanesulfonamidoethyl)tetrazol-5-ylthiomethyl]-3-cephem-4-carboxylic acid.

EXAMPLE 8

7β-Amino-3-[1-(2-methanesulfonamidoethyl)tetrazol-5-ylthiomethyl]-3-cephem-4-carboxylic acid A solution of 13.62 g (0.06 mol) of 1-(2-methanesulfonamidoethyl)tetrazole-5-thiol in 120 ml of acetone is added to a warm (45°) solution of 10.9 g (0.04 mol) of 7-aminocephalosporanic acid in a mixture of 220 ml of water, 50 ml of acetone and 8.4 g (0.01 mol) of sodium bicarbonate. The temperature is raised to 65° and the pH maintained at 7.4–7.6 by addition of aqueous sodium carbonate solution. After 3 hours, the acetone is removed in vacuo and the reaction mixture is cooled to 10° and adjusted to pH 3.5 by addition of dilute hydrochloric acid. The product is collected, washed with water and then acetone to give the title compound.

EXAMPLE 9

7β-(2,2,2-Trifluoroethylsulfinylacetamido)-3-[1-(2-methanesulfonamidoethyl)tetrazol-5-ylthiomethyl]-3-cephem-4-carboxylic acid To a stirred solution of 5.7 g (0.03 mol) of 2,2,2-trifluoroethylsulfinylacetic acid and 3.45 g (0.03 mol) of N-hydroxysuccinimide in 50 ml of tetrahydrofuran at 0° is added 6.2 g (0.031 mol) of dicyclohexylcarbodiimide. The reaction mixture is stirred at 0° for 1 hour then at 25° for 12 hours. The precipitate is filtered and washed with tetrahydrofuran and the filtrate is evaporated to dryness to give the activated ester of 2,2,2-trifluoroethylsulfinylacetic acid.

A suspension of 4.35 g (0.01 mol) of 7β-amino-3-[1-(2methanesulfonamidoethyl)tetrazol-5-ylthiomethyl]-3-cephem-4-carboxylic acid in 50 ml of dry dimethylformamide is treated with 2 ml of triethylamine and the mixture is stirred for 15 minutes at 25°. A slight excess of 0.01 mol of the activated ester of 2,2,2-trifluoroethylsulfinylacetic acid is added to the mixture and it is stirred an additional hour. The reaction mixture is evaporated to dryness and water and ethyl acetate are added to the residue. The layers are separated, the ethyl acetate layer is discarded, fresh ethyl acetate is added to the aqueous phase and it is acidified to pH 2.5 by addition of 6N hydrochloric acid. The mixture is filtered, the layers are separated and the aqueous phase is extracted with ethyl acetate. The combined extracts are washed with water, dried ($MgSO_4$) and evaporated to dryness to give the title compound.

EXAMPLE 10

7β-Methylthioacetamido-3-[1-(2-methanesulfonamidoethyl)-tetrazol-5-ylthiomethyl]-3-cephem-4-carboxylic acid To a stirred, cooled (−20°) solution of 11.32 g (0.026 mol) of 7-amino-3-[1-(2-methanesulfonamidoethyl)tetrazol-5-ylthiomethyl]-3-cephem-4-carboxylic acid in 220 ml of 3% sodium bicarbonate and 220 ml of acetone is added dropwise a solution of 3.66 g (0.029 mol) of methylthioacetyl chloride in 52 ml of acetone, during which time the pH of the reaction mixture is maintained at 8.0 by addition of 10% sodium hydroxide. After addition the reaction mixture is stirred an additional 20 minutes at −15°, then is warmed to 25° and extracted with ether. The remaining aqueous phase is cooled, 250 ml of ethyl acetate is added and the slurry is acidified with 3N hydrochloric acid. The layers are separated and the aqueous phase is extracted twice more with ethyl acetate. The combined extracts are dried (MgSO$_4$) and evaporated to dryness to yield the title compound.

EXAMPLE 11

7β-(D-α-Formyloxyphenylacetamido)-3-[1-methanesulfonamidoethyl)tetrazol-5-ylthiomethyl]-3-cephem-4-carboxylic acid A mixture of 4.35 g (0.01 mol) of 7-amino-3-[1-(2-methanesulfonamidoethyl)tetrazol-5-ylthiomethyl]-3-cephem-4-carboxylic acid, 3.97 g (0.02 mol) of the formate ester of D-mandeloyl chloride and 5 g of sodium bicarbonate in 100 ml of water and 140 ml of acetone is stirred in the cool for 1 hour, then at 25° for 2 hours. The acetone is evaporated in vacuo and the remaining aqueous mixture is extracted with ethyl acetate. The aqueous solution is added with stirring to a cold mixture of 100 ml of water and 200 ml of ethyl acetate and the pH of the resulting mixture is adjusted to 2.0 by addition of 6N hydrochloric acid. The mixture is filtered, the layers are separated and the ethyl acetate layer is washed with water, dried (MgSO$_4$) and evaporated to dryness to give the title compound.

EXAMPLE 12

Acylation of 7β-amino-3-[1-(2-methanesulfonamidoethyl)tetrazol-5-ylthiomethyl]-3-cephem-4-carboxylic acid with an activated derivative of an acid listed below:
cyanoacetic acid
cyanomethylthioacetic acid
4-pyridylthioacetic acid
2-pyridone-N-acetic acid
4-pyridone-N-acetic acid
as described in the procedure of Example 9 gives the following compounds of this invention:
7β-cyanoacetamido-3-[1-(2-methanesulfonamidoethyl)-tetrazol-5-ylthiomethyl]-3-cephem-4-carboxylic acid
7β-cyanomethylthioacetamido-3-[1-(2-methanesulfonamidoethyl)tetrazol-5-ylthiomethyl]-3-cephem-4-carboxylic acid
7β-(4-pyridylthioacetamido)-3-[1-(2-methanesulfonamidoethyl)tetrazol-5-ylthiomethyl]-3-cephem-4-carboxylic acid
7β-(2-pyridoneacetamido)-3-[1-(2-methanesulfonamidoethyl)tetrazol-5-ylthiomethyl]-3-cephem-4-carboxylic acid
7β-(4-pyridoneacetamido)-3-[1-(2-methanesulfonamidoethyl)tetrazol-5-ylthiomethyl]-3-cephem-4-carboxylic acid.

EXAMPLE 13

Reaction of a cephalosporanic acid listed below or its corresponding salt:
7β-(α-hydroxy-2-thienylacetamido)cephalosporanic acid
7β-(α-carboxy-2-thienylacetamido)cephalosporanic acid
7β-(α-sulfophenylacetamido)cephalosporanic acid with 1-(2-methanesulfonamidoethyl)tetrazol-5-thiol and sodium bicarbonate by procedures described hereinabove gives, after conversion of the product to the free acid, the following compounds of this invention:
7β-(α-hydroxy-2-thienylacetamido)-3-[1-(2-methanesulfonamidoethyl)tetrazol-5-ylthiomethyl]-3-cephem-4-carboxylic acid
7β-(α-carboxy-2-thienylacetamido)-3-[1-(2-methanesulfonamidoethyl)tetrazol-5-ylthiomethyl]-3-cephem-4carboxylic acid
7β-(α-sulfophenylacetamido)-3-[1-(2-methanesulfonamidoethyl)tetrazol-5-ylthiomethyl]-3-cephem-4-carboxylic acid.

EXAMPLE 14

7β-(2,2,2-Trifluoroethylsulfonylacetamido)-3-[1-(2-methanesulfonamidoethyl)tetrazol-5-ylthiomethyl]-3-cephem-4-carboxylic acid To a suspension of 21.8 g (0.05 mol) of 7β-amino-3-[1-(2-methanesulfonamidoethyl)tetrazol-5-ylthiomethyl]-3-cephem-4-carboxylic acid in 500 ml of methylene chloride is added over a 30 minute interval a solution of 30.0 g (0.15 mol) of O-t-butyldiisopropylpseudourea in 100 ml of methylene chloride. The mixture is stirred at ambient temperature for 72 hours. The precipitate is removed by filtration and the filtrate is evaporated to a residue which is taken up in 200 ml of benzene and filtered again. The filtrate is extraced with three 100 ml portions of cold 1N hydrochloric acid. The aqueous extracts are layered with ethyl acetate and the pH is adjusted to 7.5 by addition of solid sodium bicarbonate. The organic layer is separated and the aqueous phase extracted with two 150 ml portions of ethyl acetate. The combined extracts are dried (MgSO$_4$), filtered and evaporated to dryness to give 7β-amino-3-[1-(2-methanesulfonamidoethyl)tetrazol-5-ylthiomethyl]-3-cephem-4-carboxylic acid t-butyl ester.

To a solution of 9.34 g (0.019 mol) of 7-amino-3-[1-(2-methanesulfonamidoethyl)tetrazol-5-ylthiomethyl]-3-cephem-4-carboxylic acid t-butyl ester and 3.9 g (0.019 mol) of 2,2,2-trifluoroethylsulfonylacetic acid in tetrahydrofuran is added dropwise a solution of 3.9 g (0.019 mol) of dicyclohexylcarbodiimide in 100 ml of tetrahydrofuran. The reaction mixture is stirred at 25° for 12 hours, then filtered and concentrated to about 10 ml. The residue is filtered and evaporated to dryness to give 7β-(2,2,2-trifluoroethylsulfonylacetamido)-3-[1-(2-methanesulfonamidoethyl)tetrazol-5-ylthiomethyl[-3-cephem-4-carboxylic acid t-butul ester.

The ester is dissolved in acetonitrile and trifluoroacetic acid is added. The solution is stirred for 3 hours, then evaporated to dryness to give the title compound.

Likewise, 7β-(2,2,2-trifluoroethylsulfonylacetamido) derivatives of the other 7β-amino-3-substituted tetrazole cephalosporins disclosed herein are prepared.

EXAMPLE 15

When an equivalent amount of a N-aminoalkylacetamide listed below:
N-(3-aminopropyl)acetamide
N-(4-aminobutyl)acetamide
N-(5-aminopentyl)acetamide
is used in the procedure of Example 1 in place of N-(2-aminoethyl)acetamide and the resulting dithiocarbamates are treated with sodium azide to produce the corresponding 1-acetamidoalkyltetrazole-5-thiols which are converted to the 1-methanesulfonamidoalkyl derivatives, all as described therein, the following 1- methanesulfonamidoalkyltetrazole-5-thiols are obtained:
1-(3-methanesulfonamidopropyl)tetrazole-5-thiol
1-(4-methanesulfonamidobutyl)tetrazole-5-thiol
1-(5-methanesulfonamidopenty)tetrazole-5-thiol.

Reaction of a 1-methanesulfonamidoalkyltetrazole-5-thiol listed above with 7β-D-mandelamidocephalosporanic acid sodium salt and sodium bicarbonate as described in the procedure of Example 1 followed by conversion of the salt formed to the free acid, gives the following compounds of this invention:

7β-D-mandelamido-3-[1-(3-methanesulfonamidopropyl)-tetrazol-5-ylthiomethyl]-3-cephem-4-carboxylic acid
7β-D-mandelamido-3-[1-(4-methanesulfonamidobutyl)-tetrazol-5-ylthiomethyl]-3-cephem-4-carboxylic acid
7β-D-mandelamido-3-[1-(5-methanesulfonamidopentyl)-tetrazol-5-ylthiomethyl]-3-cephem-4-carboxylic acid.

Likewise, reaction of the substituted tetrazole thiols listed above with any of the 7β-acyl cephalosporanic acids mentioned herein or their corresponding salts according to procedures described herein gives the corresponding compounds of this invention.

EXAMPLE 16

When ethanesulfonyl chloride, propanesulfonyl chloride or butanesulfonyl chloride is substituted for methanesulfonyl chloride in the reaction with 1-(2-aminoethyl)-5-(2,4-dinitrophenylthio)tetrazole hydrochloride described in Example 1 and the product thus formed is treated with sodium methoxide also as described therein, the following 1-(2-alkanesulfonamidoethyl)tetrazole-5-thiols are prepared, respectively:
1-(2-ethanesulfonamidoethyl)tetrazole-5-thiol
1-(2-propanesulfonamidoethyl)tetrazole-5-thiol
1-(2-butanesulfonamidoethyl)tetrazole-5-thiol.

Reaction of 7β-D-mandelamidocephalosporanic acid sodium salt, a 1-(2-alkanesulfonamidoethyl)tetrazole-5-thiol listed above and sodium bicarbonate as described in Example 1 followed by conversion of the salt formed to the free acid gives the following compounds of this invention:

7β-D-mandelamido-3-[1-(2-ethanesulfonamidoethyl)-tetrazol-5-ylthiomethyl]-3-cephem-4-carboxylic acid
7β-D-mandelamido-3-[1-(2-propanesulfonamidoethyl)-tetrazol-5-ylthiomethyl]-3-cephem-4-carboxylic acid
7β-D-mandelamido-3-[1-(2-butanesulfonamidoethyl)-tetrazol-5-ylthiomethyl]-3-cephem-4-carboxylic acid.

EXAMPLE 17

7β-Cyanoacetamido-7α-methoxy-3-[1-(2-methanesulfonamidoethyl)tetrazol-5-ylthiomethyl]-3-cephem-4-carboxylic acid A solution of 1.18 g (2.4 mmol) of 7β-amino-3-[1-(2-methanesulfonamidoethyl)tetrazol-5-ylthiomethyl]-3-cephem-4-carboxylic acid t-butyl ester and 0.56 g (2.4 mmol) of 3,5-di-t-butyl-4-hydroxybenzaldehyde in 100 ml of dry benzene is refluxed for 4 hours under a Dean-Stark trap. The solution is evaporated under reduced pressure to leave a residue which is dissolved in 100 ml of 1,2-dichloroethane and cooled to ca. 5° in an ice bath. Three grams of freshly prepared lead dioxide is added in portions over 20 minutes until the starting material is completely consumed. The mixture is filtered through Celite and the filter cake is washed with two 20 ml portions of cold 1,2-dichloroethane. The filtrate is treated with 25 ml of methanol (distilled from magnesium) and the reaction mixture is allowed to stand at room temperature until complete consumption of the oxidized intermediate and formation of a new slower-moving product is shown by thin layer chromatography. The mixture is evaporated and the residue is dissolved in 30 ml of methanol and treated with 2.5 g of Girard reagent T (trimethylaminoacetohydrazide chloride). The reaction mixture is stirred at room temperature for 3 hours, then evaporated to give a residue which is partitioned between ethyl acetate and 20% sodium chloride solution. The organic phase is washed with 10% sodium chloride solution water and a saturated sodium chloride solution. The organic phase is dried (MgSO$_4$), filtered and evaporated to dryness to give 7β-amino-7α-methoxy-3-[1-(2-methanesulfonamidoethyl)tetrazol-5-ylthiomethyl]-3-cephem-4-carboxylic acid t-butyl ester.

A solution of 2.09 g (4 mmol) of 7β-amino-7α-methoxy-3-[1-(2-methanesulfonamidoethyl)tetrazol-5-ylthiomethyl]-3-cephem-4-carboxylic acid t-butyl ester and 0.60 g (4 mmol) of N,N-diethylaniline in 100 ml of dry methylene chloride is stirred at 0°–5° while 0.41 g (4 mmol) of cyanoacetyl chloride in 20 ml of methylene chloride is added over a 10 minute period. The mixture is stirred in the cold for 30 minutes and then at ambient temperature for an additional 30 minutes. The reaction mixture is washed with 100 ml of dilute hydrochloric acid, 100 ml of 5% sodium bicarbonate and water. The organic phase is dried and evaporated to give a residue which is dissolved in 20 ml of 2:1 trifluoroacetic acid-m-dimethoxybenzene and stirred for 3 hours. Excess trifluoroacetic acid is evaporated and the residue is added to 200 ml of rapidly stirred ether. The resulting precipitate is collected, washed well with ether and dried to give the title compound.

EXAMPLE 18

7β-(D-α-aminophenylacetamido)-7α-methoxy-3-[1-(2-methanesulfonamidoethyl)tetrazol-5-ylthiomethyl]-3-cephem-4-carboxylic acid To a solution of 2.09 g (4 mmol) of 7β-amino-7α-methoxy-3-[1-(2-methanesulfonamidoethyl)tetrazol-5-ylthiomethyl]-3-cephem-4-carboxylic acid t-butyl ester and 1.00 g (4 mmol) of D-α-(N-t-butoxycarbonyl)-phenylglycine in 50 ml of dry tetrahydrofuran is added 0.82 g (4 mmol) of dicyclohexylcarbodiimide. The mixture is stirred at ambient temperature for 3 hours. The precipitated urea is removed by filtration and the solvent is evaporated to leave a residue which is taken up in 100 ml of chloroform and washed with 100 ml portions of dilute hydrochloric acid, 5% aqueous sodium bicarbonate and water. The organic layer is separated, dried and evaporated to give a residue which is dissolved in 20 ml of 2:1 trifluoroacetic acid-m-dimethoxybenzene and stirred for three hours. Excess trifluoroacetic acid is evaporated under vacuum and the residue is added dropwise to 300 ml of rapidly stirred ether. The precipitate is removed by filtration, washed with ether and dried to give the title compound as its trifluoroacetic acid salt.

An aqueous solution of the trifluoroacetic acid salt is treated with Amberlite IR-45 weakly basic ion exchange resin and then lyophilized to give the title compound.

EXAMPLE 19

7β-D-Mandelamido-7α-methoxy-3-[1-(2-methanesulfonamidoethyl)tetrazol-5-ylthiomethyl]-3-cephem-4-carboxylic acid A solution of 1.04 g (2 mmol) of 7β-amino-7α-methoxy-3-[1-(2-methanesulfonamidoethyl)tetrazol-5-ylthiomethyl]-3-cephem-4-carboxylic acid t-butyl ester and 0.30 g (2 mmol) of N,N-diethylaniline in 100 ml of dry methylene chloride is stirred at 0°–5° while 0.56 g (2 mmol) of D-O-dichloroacetylmandeloyl chloride in 10 ml of methylene chloride is added dropwise over 10 minutes. The mixture is stirred in the cold for 30 minutes when warmed to room temperature and stirred for an additional 30 minutes. The solution is washed with 50 ml of cold dilute hydrochloric acid and 50 ml of cold 5% aqueous sodium bicarbonate, dried and evaporated to dryness. The residue is dissolved in a mixture of 10 ml of trifluoroacetic acid and 2 ml of m-dimethoxybenzene and stirred at ambient temperature for 2 hours. The excess trifluoroacetic acid is evaporated under vacuum and the residue is partitioned between 50 ml of ether and 50 ml of water and adjusted to pH 9.3–9.5 with 5% aqueous sodium carbonate. The organic phase is separated and discarded. The aqueous phase is stirred at pH 9.3–9.5 for 30 minutes, extracted with 50 ml of ethyl acetate which is discarded, layered with fresh ethyl acetate and adjusted to pH 1.5 with dilute hydrochloric acid. The aqueous layer is extracted with three 50 ml portions of ethyl acetate and the combined extracts are dried and evaporated to a small volume. Petroleum ether is added dropwise to precipitate the title compound which is collected by filtration and dried.

EXAMPLE 20

7α-Methoxy-7β-(2-thienylacetamido)-3-[1-(2-methanesulfonamidoethyl)tetrazol-5-ylthiomethyl]-3-cephem-4-carboxylic acid A solution of 1.28 g (3 mmol) of 7α-methoxy-7β-(2-thienylacetamido)cephalosporanic acid sodium salt is dissolved in 50 ml of water, 1.02 g (4.5 mmol) of 1-(2-methanesulfonamidoethyl)tetrazole-5-thiol and sufficient sodium bicarbonate to bring the pH to 6.8 are added and the solution is heated at 70° until thin layer chromatography indicates consumption of the starting material (ca. 5 hours). After cooling to ambient temperature, the reaction mixture is covered with ethyl acetate and acidified with 3N hydrochloric acid to pH 1.8. The layers are separated and the aqueous phase is extracted with ethyl acetate. The combined organic phases are dried (MgSO₄) and evaporated in vacuo to give the title compound.

EXAMPLE 21

7α-Methoxy-7β-trifluoromethylthioacetamido-3-[1-(2-methanesulfonamidoethyl)tetrazol-5-ylthiomethyl]-3-cephem-4-carboxylic acid To a cold solution of 5.25 g (0.012 mol) of 7β-amino-7α-methoxycephalosporanic acid benzhydryl ester in 200 ml of methylene chloride containing 1.79 g (0.012 mol) of N,N-diethylaniline is added dropwise over a 20 minute period a solution of 1.82 g (0.012 mol) of trifluoromethylthioacetyl chloride in 50 ml of methylene chloride. After stirring for 30 minutes, the mixture is extracted successively with 5% aqueous sodium bicarbonate, 5% aqueous hydrochloric acid and finally with brine. The organic phase is dried (MgSO₄) and the solvent evaporated to give 7α-methoxy-7β-trifluoromethylthioacetamidocephalosporanic acid benzhydryl ester.

7α-Methoxy-7β-trifluoromethylthioacetamidocephalosporanic acid benzhydryl ester is dissolved in a cold mixture of trifluoroacetic acid-anisole (2:1) and the mixture is stirred for 1.5 hours without external cooling. The solvent is evaporated in vacuo and the residual product is taken up in ethyl acetate, washed with water, dried (MgSO₄) and concentrated in vacuo to a small volume. This solution is added dropwise to stirred petroleum ether to yield 7α-methoxy-7β-trifluoromethylthioacetamidocephalosporanic acid.

7α-Methoxy-7β-trifluoromethylthioacetamidocephalosporanic acid (2.2 g, 5 mmol) is suspended in 75 ml of water and 0.4 g of solid sodium bicarbonate is added until solution is complete. To this solution is added 1.7 g (7.5 mmol) of 1-(2-methanesulfonamidoethyl)tetrazole-5-thiol and sufficient sodium bicarbonate to bring the pH to 7.5. The mixture is heated at 70° for 7 hours while maintaining the pH at 7.5. Progress of the reaction is monitored by thin layer chromatography and judged to be complete when tlc indicates disappearance of starting material (ca. 7 hours). The reaction mixture is then cooled to ambient temperature, covered with ethyl acetate and acidified to pH 1.8 with 3N hydrochloric acid. The layers are separated and the aqueous phase is extracted with ethyl acetate. The combined organic phases are dried (MgSO₄) and evaporated in vacuo to give the title compound.

EXAMPLE 22

An injectable pharmaceutical composition is formed by adding sterile water or sterile saline solution (2 ml) to 500 mg of 7β-D-mandelamido-3-[1-(2-methanesulfonamidoethyl)tetrazol-5-ylthiomethyl]-3-cephem-4-carboxylic acid sodium salt. A unit dose is administered intramuscularly to a subject infected with an organism susceptible to the compound as noted herebefore every 4 to 6 hours. Intravenous or drip administration is also similarly used.

Pharmaceutical compositions of the other antibacterial compounds disclosed above may be formulated and used in a similar manner based on their relative activities as compared with those given hereabove.

What is claimed is:

1. A compound of the formula:

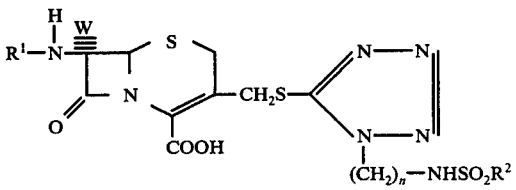

in which:

W is hydrogen or methoxy;

$R^1$ is an acyl group of the formula:

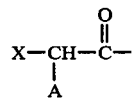

where:

X is thienyl, phenyl or phenyl monosubstituted with hydroxy, hydroxymethyl, formamido or ureido;

A is NH$_2$, OH, COOH, SO$_3$H or formyloxy;

n is two to five; and

R$^2$ is alkyl of from one to four carbon atoms, or a non-toxic pharmaceutically acceptable salt thereof.

2. A compound according to claim 1 in which A is NH$_2$.

3. A compound according to claim 1 in which A is OH.

4. A compound according to claim 1 in which A is COOH.

5. A compound according to claim 1 in which A is SO$_3$H.

6. A compound according to claim 1 in which A is formyloxy.

7. A compound according to claim 1 in which n is two.

8. A compound according to claim 7 in which R$^2$ is methyl.

9. A compound according to claim 2 in which X is phenyl or hydroxyphenyl.

10. A compound according to claim 9 in which n is two and R$^2$ is methyl.

11. A compound according to claim 10 in which W is hydrogen.

12. A compound according to claim 10 in which W is methoxy.

13. A compound according to claim 11, said compound being 7β-(α-aminophenylacetamido)-3-[1-(2-methanesulfonamidoethyl)tetrazol-5-ylthiomethyl]-3-cephem-4-carboxylic acid.

14. A compound according to claim 11, said compound being 7β-(α-amino-4-hydroxyphenylacetamido)-3-[1-(2-methanesulfonamidoethyl)tetrazol-5-ylthiomethyl]-3-cephem-4-carboxylic acid.

15. A compound according to claim 12, said compound being 7β-(α-aminophenylacetamido)-7α-methoxy-3-[1-(2-methanesulfonamidoethyl)tetrazol-5-ylthiomethyl]-3-cephem-4-carboxylic acid.

16. A compound according to claim 3 in which X is phenyl or hydroxyphenyl.

17. A compound according to claim 16 in which n is two and R$^2$ is methyl.

18. A compound according to claim 17 in which W is hydrogen.

19. A compound according to claim 17 in which W is methoxy.

20. A compound according to claim 18, said compound being 7β-mandelamido-3-[1-(2-methanesulfonamidoethyl)tetrazol-5-ylthiomethyl]-3-cephem-4-carboxylic acid.

21. A compound according to claim 18, said compound being 7β-mandelamido-3-[1-(2-methanesulfonamidoethyl) tetrazol-5-ylthiomethyl]-3-cephem-4-carboxylic acid sodium salt.

22. A compound according to claim 19, said compound being 7β-mandelamido-7α-methoxy-3-[1-(2-methanesulfonamidoethyl)tetrazol-5-ylthiomethyl]-3-cephem-4-carboxylic acid.

23. An antibacterial pharmaceutical composition comprising a compound as claimed in claim 1 and a pharmaceutically acceptable carrier therefor.

24. An antibacterial pharmaceutical composition comprising a compound as claimed in claim 29 and a pharmaceutically acceptable carrier therefor.

25. An antibacterial pharmaceutical composition comprising a compound as claimed in claimed 21 and a pharmaceutically acceptable carrier therefor.

26. A method of treating bacterial infections comprising administering internally by injection to an infected or susceptible warm-blooded animal an antibacterially effective but nontoxic dose of a compound as claimed in claim 1.

27. A method as claimed in claim 26, in which the compound is 7β-mandelamido-3-[1-(2-methanesulfonamidoethyl)tetrazol-5-ylthiomethyl]-3-cephem-4-carboxylic acid.

28. A method as claimed in claim 26, in which the compound is 7β-mandelamido-3-[1-(2-methanesulfonamidoethyl)tetrazol-5-ylthiomethyl]-3-cephem-4-carboxylic acid sodium salt.

29. A compound according to claim 18, said compound being a hydrate of 7β-mandelamido-3-[1-(2-methanesulfonamidoethyl)-tetrazol-5-ylthiomethyl]-3-cephem-4-carboxylic acid sodium salt.

30. A compound according to claim 18, said compound being 7β-D-mandelamido-3-[1-(2-methanesulfonamidoethyl)tetrazol-5-ylthiomethyl]-3-cephem-4-carboxylic acid.

* * * * *